(12) United States Patent
Chang et al.

(10) Patent No.: US 7,704,243 B2
(45) Date of Patent: Apr. 27, 2010

(54) DISPOSABLE ABSORBENT ARTICLE HAVING LEG WRAPS AND METHOD OF MAKING SAME

(75) Inventors: Kuo-Shu Edward Chang, Charlotte, NC (US); Anne Smid, Wolvega (NL); Patrick King Yu Tsang, Matlock (GB); Ian Walker, Chesterfield (GB); Andrew Wright, Chesterfield (GB)

(73) Assignee: DSG Technology Holdings Ltd., Tortola (VG)

( * ) Notice: Subject to any disclaimer, the term of this patent is extended or adjusted under 35 U.S.C. 154(b) by 0 days.

(21) Appl. No.: 11/295,781

(22) Filed: Dec. 6, 2005

(65) Prior Publication Data

US 2006/0122571 A1  Jun. 8, 2006

Related U.S. Application Data

(60) Provisional application No. 60/633,842, filed on Dec. 6, 2004.

(51) Int. Cl.
*A61F 13/15* (2006.01)
(52) U.S. Cl. .............. 604/385.24; 604/385.25; 604/385.26; 604/385.27; 604/385.28; 604/385.29
(58) Field of Classification Search ............ 604/385.24, 604/385.25, 385.26, 385.27, 385.28
See application file for complete search history.

(56) References Cited

U.S. PATENT DOCUMENTS

| | | | |
|---|---|---|---|
| 3,860,003 A | 1/1975 | Buell |
| 4,081,301 A | 3/1978 | Buell |
| 4,360,021 A | 11/1982 | Stima |
| 4,381,783 A | 5/1983 | Elias |
| 4,397,645 A | 8/1983 | Buell |
| 4,578,071 A | 3/1986 | Buell |
| 4,597,760 A | 7/1986 | Buell |
| 4,597,761 A | 7/1986 | Buell |
| 4,636,207 A | 1/1987 | Buell |
| 4,681,579 A | 7/1987 | Toussant et al. |

(Continued)

FOREIGN PATENT DOCUMENTS

EP 0 329 160 12/1982

(Continued)

OTHER PUBLICATIONS

Written Opinion of the International Search Authority (PCT/ISA/237), for related PCT application PCT/US2005/044595. 5 pages.

*Primary Examiner*—Jacqueline F. Stephens
(74) *Attorney, Agent, or Firm*—Fulbright & Jaworski LLP

(57) ABSTRACT

A leg wrap structure is provided in a disposable absorbent garment such as a diaper or training pants. The leg wrap structure has a base layer, a top layer, and an elastic construction disposed therebetween. The elastic construction includes a plurality of spaced apart (e.g. generally equally spaced apart) elastic elements (e.g. strands or threads) that are aligned in a generally in generally parallel relation. Further, the top and base layers define a region of inelasticity. The leg wrap structure provides for the efficient formation of a reservoir and a plurality of fluid dams each capable of capturing a quantity of fluid to minimize the occurrence of fluid leaks from the absorbent article. Methods of forming such absorbent articles are disclosed.

16 Claims, 16 Drawing Sheets

U.S. PATENT DOCUMENTS

| | | |
|---|---|---|
| 4,704,115 A | 11/1987 | Buell |
| 4,900,317 A | 2/1990 | Buell |
| 4,909,803 A | 3/1990 | Aziz et al. |
| 4,938,754 A | 7/1990 | Mesek |
| 5,080,658 A | 1/1992 | Igaue et al. |
| 5,085,654 A | 2/1992 | Buell |
| 5,690,627 A | 11/1997 | Clear |
| 5,904,675 A | 5/1999 | Laux et al. |
| 5,921,975 A | 7/1999 | Suzuki et al. |
| 6,706,030 B1 | 3/2004 | Okuda et al. |
| 6,764,478 B2 | 7/2004 | Ashton et al. |
| 2002/0123732 A1* | 9/2002 | Koyama et al. ........ 604/385.24 |
| 2004/0059311 A1 | 3/2004 | Minato et al. |

FOREIGN PATENT DOCUMENTS

| | | |
|---|---|---|
| GB | 2 100 130 | 8/1989 |

\* cited by examiner

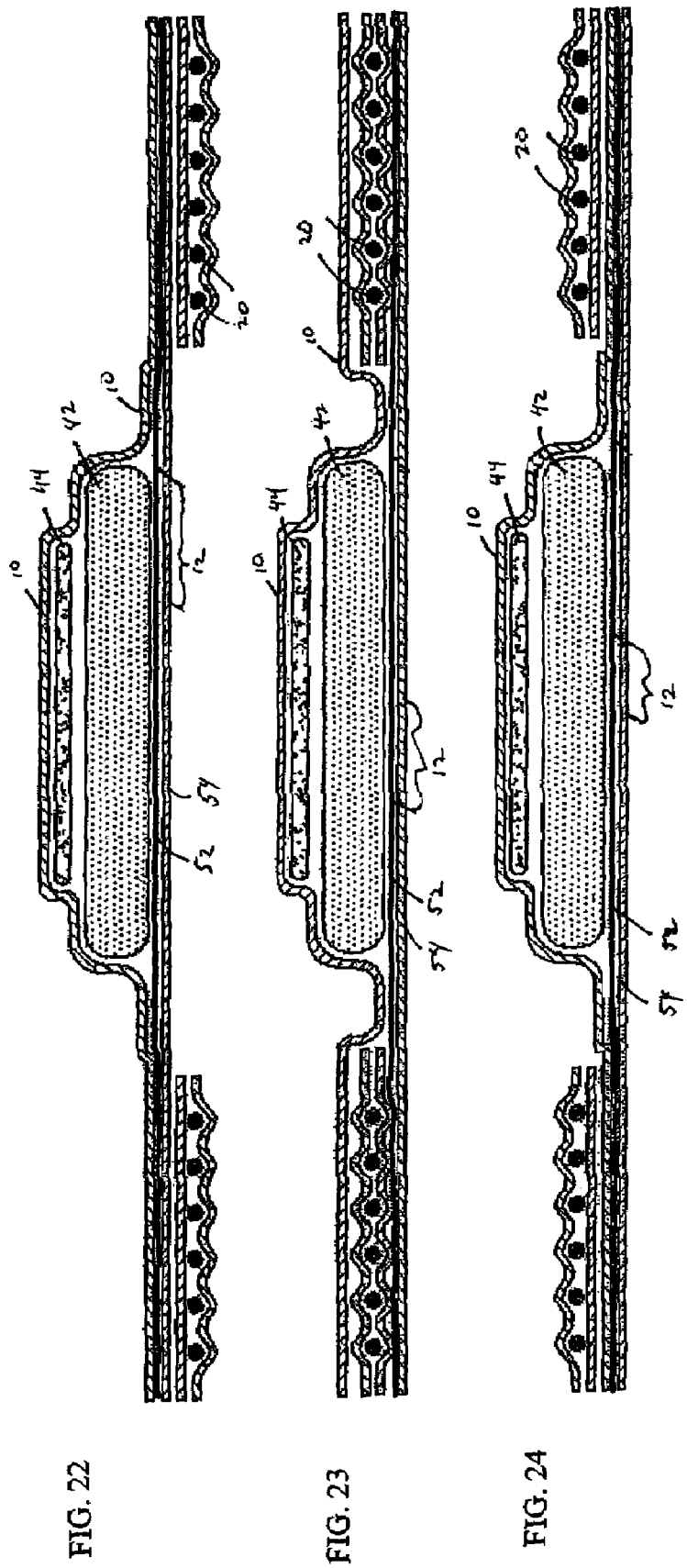

DISPOSABLE ABSORBENT ARTICLE HAVING LEG WRAPS AND METHOD OF MAKING SAME

RELATED APPLICATIONS

This application claims priority to U.S. Provisional Application No. 60/633,842 filed Dec. 6, 2004, the entire contents being incorporated herein by reference

FIELD OF THE INVENTION

The present invention relates to absorbent articles such as disposable diapers, and more particularly, to absorbent articles having elastic leg wraps capable of forming a reservoir to contain liquid and a plurality of fluid dams further capable of retaining liquid to improve the overall containment characteristics of the absorbent article, especially the containment of loose fecal material.

BACKGROUND OF THE INVENTION

Disposable absorbent articles are worn to contain and absorb urine and fecal exudates. To this end, an absorbent article incorporates certain components or structural attributes which function to provide a close, comfortable fit around the user's legs and waist. Such a close fit enhances the containment and leakage prevention capabilities of the absorbent article.

Typical principle elements of disposal absorbent articles include a liquid-permeable inner layer or topsheet, a liquid-impermeable outer layer or backsheet, and an absorbent core sandwiched between the inner and outer layers. Elasticized barrier leg cuffs, gathering components, and waistbands are often employed to provide leakage prevention by enhancing the fit of the absorbent article about the thighs and waist of the user. For example, elastic members may be positioned longitudinally along the article, generally outboard of the absorbent core to effect a seal around the legs of the user. In addition, several elastic members e.g., in the form of elongated elastic threads or strands may be positioned laterally throughout the waist regions including side waist regions of the disposable absorbent article to allow the article to stretch during use. In this way, the article can stretch to accommodate variations of waist size and leg size of the user, while maintaining a proper fit and leg seal during use.

The major function of absorbent articles such as disposable diapers and adult incontinent briefs is to absorb and contain body exudates. Such articles are intended to prevent body exudates from soiling, wetting, or otherwise contaminating clothing or other articles, such as bedding, that come in contact with the wearer. A limitation of such products is leakage out of the leg seals between the absorbent article and the wearer's leg or waist and onto adjacent clothing. This is most evident with loose fecal material which is not easily absorbed by the absorbent article and tends to freely flow on the top surface of the absorbent article.

Contemporary disposable diapers have elasticizied leg cuffs to improve both wearing comfort and the ability to contain body exudates. These elasticized leg cuffs prove somewhat effective to prevent wicking and overflow from a fluid laden absorbent article to clothing contacting the edges of the article in that the elasticized leg flaps present a fluid impervious barrier between the edge of the absorbent core and the contacting clothing, and in addition, provide for a sealing action about the legs of the wearer. Despite the effectiveness of such structures, however, body exudates, especially loose fecal material, can leak through the elasticized leg cuffs and soil the wearer's clothing because the diaper does not constrain the free flow of such material nor provide a structure to hold it within the diaper so that as such material flows along the top surface of the topsheet, it tends to work its way past the elasticized leg cuffs.

Thus, it would be beneficial to provide an absorbent article designed to sustain the proper fit of the article around the legs of the wearer. If would be of further benefit to provide an absorbent article having a reduced possibility of leakage at the legs. Additionally, it would be of benefit to provide an absorbent article having easy application and/or removal and improved comfort for the wearer.

SUMMARY OF THE INVENTION

The present invention relates generally to a disposable absorbent article or garment and a method of making same. More particularly, the invention relates to a disposable absorbent article, such as a baby diaper or disposable pull-on garment, that includes a pair of elasticized leg wraps for preventing liquid and/or solid exudate leakage and providing better fit and aesthetic appearance. Embodiments of the present invention provide an absorbent article having improved containment characteristics.

In one aspect of the present invention, a disposable absorbent article has a central body and a pair of elasticized leg wraps. The central body includes an absorbent core and, thus, may be referred to herein as a central absorbent assembly. When disposed in a generally flat, open condition, e.g., before being worn by a user or at a later stage in the manufacturing process, the central body has or is otherwise further characterized by a front longitudinal edge, a rear longitudinal edge opposite the front longitudinal edge, and a longitudinal centerline extending across the front and rear edges. These front and rear edges define, at least partially, front and rear waist portions, respectively, of the disposable absorbent article. The pair of elasticized leg wraps extends longitudinally adjacent opposite lateral sides of the central body. Each leg wrap is spaced outwardly from the lateral edge of the absorbent core.

In another aspect of the invention, leg wraps incorporated with or into the inventive disposable absorbent article may be characterized by an elastic stretch property or elasticity in the longitudinal direction. This elasticity is imparted to the leg wrap by an arrangement of elastic elements extending longitudinally along the disposable absorbent article. The elasticity of the leg wraps enhances the fit of the disposable absorbent article around the thighs of the user. In a particular embodiment, the elastic elements are parallel and spaced apart from each other, for example, by at least a few millimeters. In a preferred embodiment of the invention, the leg wrap provides an effective sealing function e.g., of a barrier leg cuff and leg gathers and fit function, for the disposable absorbent article.

In yet another aspect of the invention, a method of manufacturing a disposable absorbent article is provided. The method includes the step of providing a central body assembly that includes an absorbent core and providing a pair of elasticized leg wraps defined, for example, by a top layer, a bottom layer and a plurality of elastic elements between the top and bottom layers.

The present invention, in addition to providing space between the absorbent core and the leg wraps to form a reservoir, provides sufficient elastic resistance to wrap around the leg to form multiple seal and dam structures. In addition, the elastication of the leg wraps causes the leg wraps to fold itself between the upper thigh and the body and seal itself around the leg of the wearer, thus conforming to the shape of the wearer. As a result, each of the elastic leg wraps creates an effective against exudate leakage.

It is a further object of the present invention to provide an absorbent article having a reservoir and improved elasticized leg wraps defining a plurality of fluid dams so as to provide a dual restraint against the lateral flow of body exudates, thereby improving the containment characteristics of the absorbent article, especially in regard to loose fecal material.

It is also an object of the present invention to provide an absorbent article having increased comfort for the wearer and a better initial fit on the wearer.

These and other objects of the invention will be more readily apparent when considered in reference to the following description and when taken in conjunction with the accompanying drawings.

Still other embodiments of the inventive disposable article and their manufacturing methods will become readily apparent to those skilled in the relevant art from the following detailed description of the drawings, wherein the various embodiments of the invention are described by way of illustrating the best mode contemplated for carrying out the invention. The invention is capable of other and different embodiments, its several details are capable of modification and its several structural or processed details are capable of modification in various and obvious respects, all without departing from the spirit and the scope of the present invention. Accordingly, the following drawings and detailed description of the drawings are to be regarded as illustrative in nature and not restrictive.

BRIEF DESCRIPTION OF THE DRAWINGS

FIGS. 9 to 24 are cross-sectional views of various embodiments of absorbent articles similar to FIGS. 1 and 2.

DETAILED DESCRIPTION OF THE INVENTION

Figure 1:
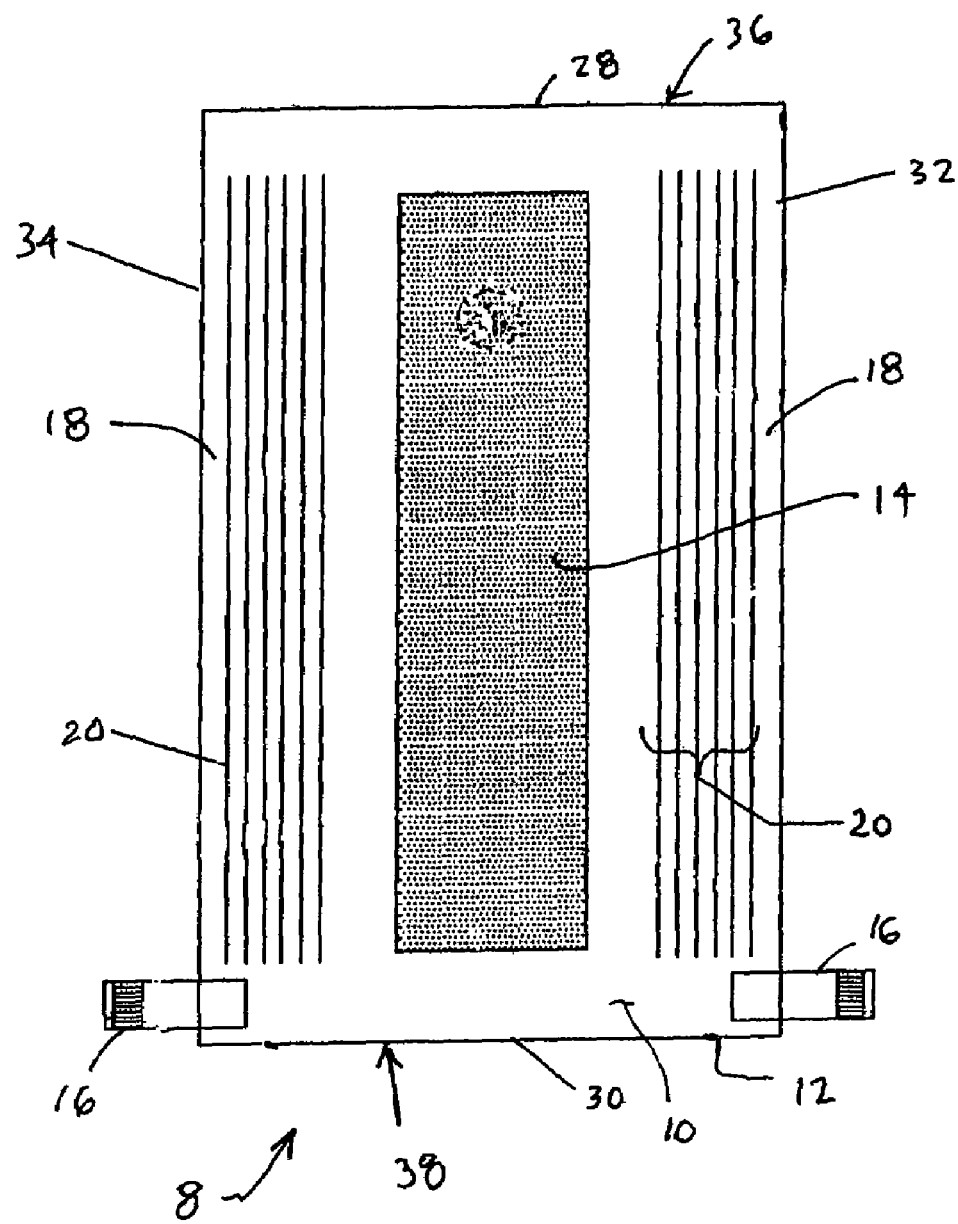
FIG. 1 is a plan view of an inside face of a disposable absorbent article in a generally flat, open condition, according to the present invention.

As used herein, the term "disposable absorbent article" refers to articles which absorb and contain body exudates and more specifically refers to articles which are placed against or in proximity to the body of the wearer to absorb and contain the various exudates discharged from the body, and to articles which are intended to be discarded after a single use (i.e., they are not intended to be laundered or otherwise restored or reused). A preferred embodiment of the disposable absorbent article of the present invention, as indicated by numeral 8, is shown in FIG. 1. As used herein, the term "absorbent article" refers to a garment generally worn by infants and incontinent persons, which is worn about the lower torso of the wearer. It should be understood, however, that the present invention is also applicable for use in other disposable absorbent articles such as incontinent briefs and the like.

FIG. 1 is a plan view of the absorbent article 8 of the present invention in the flat-out, uncontracted state (i.e., with all elastic induced contraction removed and prior to any folding operation performed on the article) with the portion of the absorbent article which contacts the wearer facing the viewer. The absorbent article 8 comprises a liquid pervious topsheet or coverstock 10; a liquid impervious backsheet 12, an absorbent core assembly 14 disposed, for example, between the coverstock 10 and the backsheet 12; a pair of fasteners 16; flexible elastic leg wraps 18; elastic members 20 secured within the leg wraps 18 and capable of defining a plurality of fluid dams 90 when worn (FIG. 28); securing means such as adhesive spots 94 (FIGS. 29-33) for securing together portions of the absorbent article, such as the coverstock 10, so as to form a reservoir 26 (not shown in FIG. 1) capable of capturing body exudates during use. The liquid pervious coverstock 10, absorbent core 14 and liquid impervious backsheet 12 may be assembled in a variety of well known configurations as appreciated by those of ordinary skill in the art.

Figure 2:
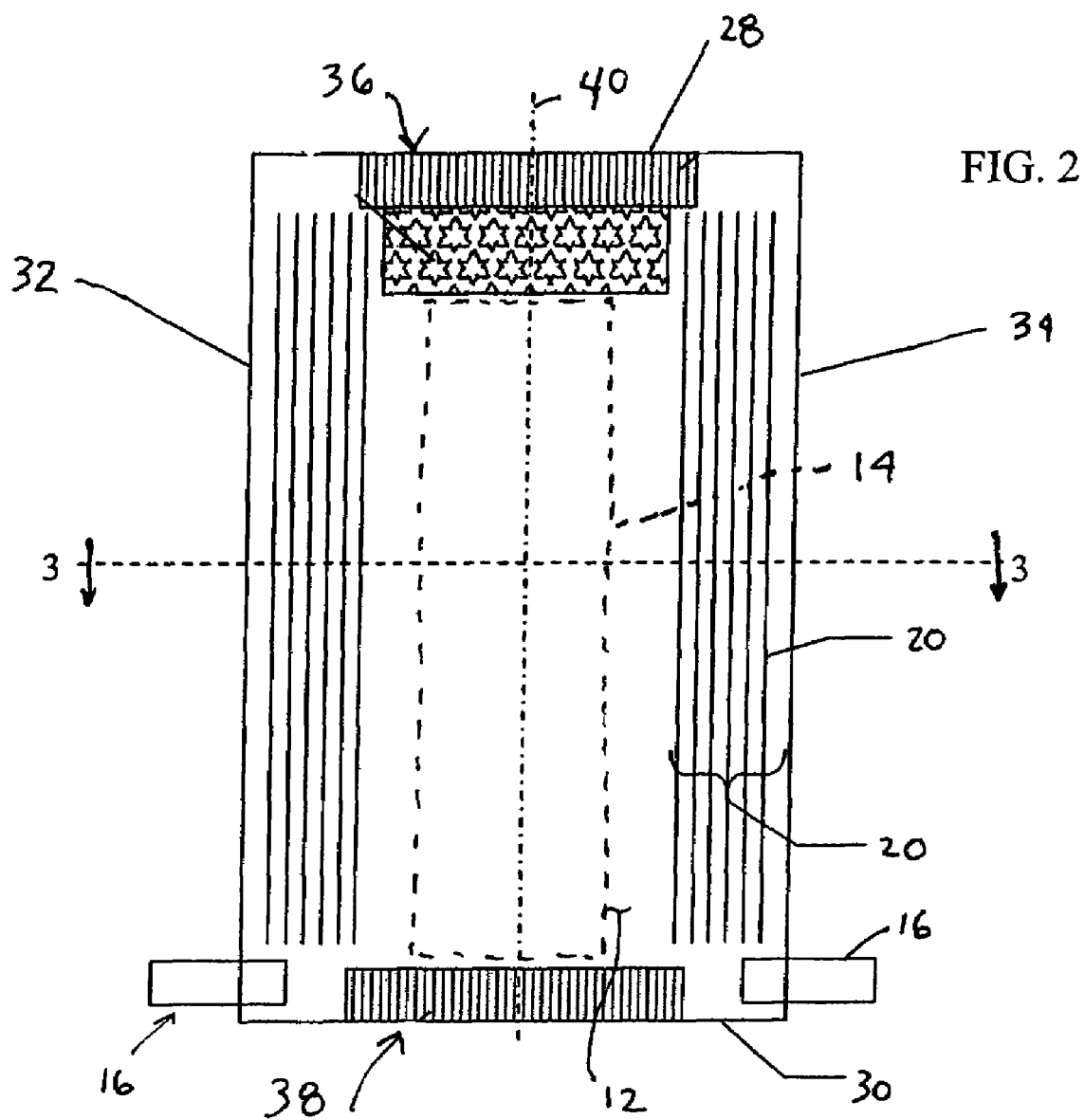
FIG. 2 is a plan view of the outside face of the disposable absorbent article of FIG. 1.

FIGS. 1-2 show a preferred embodiment of the absorbent article 8 in which the coverstock 10 and the backsheet 12 are coextensive and have length and width dimension generally larger than those of the absorbent core assembly 14. The coverstock 10 is superposed on the backsheet 12 thereby forming a periphery of the absorbent article 8 comprising end edges 28 and 30, and longitudinal edges 32 and 34.

The absorbent article 8 has waist regions 36 and 38 extending, respectively, from the end edges 28 and 30, of the absorbent article periphery toward the lateral centerline 40 of the absorbent article 8 a distance of from about ¼ to about ⅓ the length of absorbent article 8. The waist regions 36 and 38 comprise those portions of the absorbent article 8 which, when worn, is positioned between the legs of the wearer and covers the lower torso of the wearer.

Figure 3:
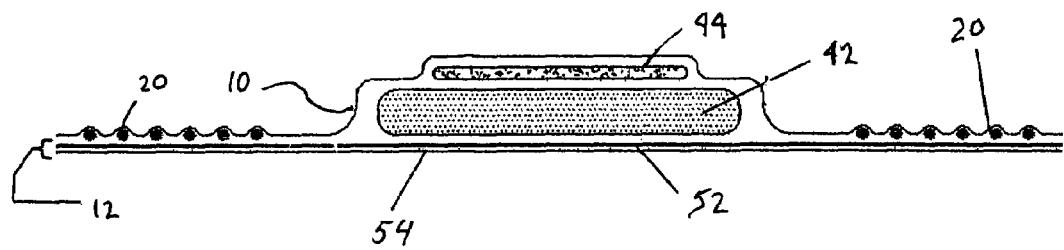
FIG. 3 is a cross-sectional view of the article of FIGS. 1 and 2 along axis 3-3.

Referring to FIG. 3, the absorbent core assembly 14 includes an absorbent core 42, a liquid permeable nonwoven coverstock 10 and a liquid impermeable backsheet 12. Additional layers of a material, such as additional absorbents, cellulose materials or nonwoven 44, that provide additional functionality such as storage of urine, fast acquisition of urine and/or distribution of urine, may also be provided within the core assembly. The absorbent core 42 may be composed of combinations of cellulose based absorbent materials, superabsorbent polymers, synthetic nonwoven materials or other absorbent materials. The disposable, absorbent article 8 is joined together in such a way that the coverstock 10 and backsheet materials 12 entirely enclose the absorbent core 42. The coverstock 10 and backsheet 12 may be directly joined together or indirectly joined together through an intermediate portion. Materials suitable for each of the core 42, coverstock 10 and backsheet 12 are generally known in the art. Descriptions of some materials and configurations suitable for use with the present invention are found in PCT International Application WO 00/03670 published Jan. 27, 2000, hereby incorporated by reference and made a part of the present disclosure.

The nonwoven coverstock 10 provides a fluid permeable upper layer of the absorbent core assembly to contain the absorbent core components and allows the passage of body exudates into the absorbent core 42 during use. Preferably coverstock 10 has length and width dimensions greater than that of the absorbent core assembly 42. These extended side edges of a nonwoven coverstock 10 may extend to the lateral edges 32, 34 of the absorbent article and serve to provide the upper layer of the composite containing the elastic members 20. The lateral sides of a nonwoven coverstock 10, which extend over the elastic leg wraps 18, may or may not be permeable to aqueous fluids.

The coverstock 10 is compliant, soft feeling, and non-irritating to the wearer's skin. Further, the coverstock 10 is liquid pervious permitting liquids to readily penetrate through its thickness. A suitable coverstock may be manufactured from a wide range of materials, such as porous foams, reticulated foams, apertured plastic films, natural fibers (e.g., wood or cotton fibers), synthetic fibers (e.g., polyester or polypropylene fibers) or from a combination of natural and synthetic fibers. Preferably, it is made of a hydrophobic material to isolate the wearer's skin from fluids in the absorbent core 42.

A further embodiment of this invention involves the use of a coverstock with zones of differing hydrophilic nature achieved by selective treatment of the material with agents which impart a hydrophilic nature to the nonwoven, e.g. surfactants. In this embodiment the coverstock will have a hydrophilic zone in the centre of the sheet, this central zone aligned to correspond with the region of the article where the absorbent core is disposed. The side zones, laterally adjacent to this central zone, may be less hydrophilic or more hydrophobic than the central zone. This produces an article having a hydrophilic, water permeable coverstock above the absorbent core to allow passage of urine into the core, and hydrophobic, water impermeable regions of said coverstock above the leg gathers to provide a dry feeling around the legs and to resist leakage of fluid through the leg wraps 18.

Leg wraps 18 may include multiple elastic strands 20 associated with each side leg panel 18. In one embodiment, elastic strands 20 are sandwiched between the nonwoven coverstock 10 and the backsheet laminate 12. The composite of the elastic strands 20, nonwoven coverstock 10 and backsheet laminate 12 is secured by using any suitable means familiar to those skilled in the art, such as adhesive bonding using slot coat or spray, spiral or swirl application of hot melt adhesive or ultrasonic bonding. In one embodiment six elastic strands 20 are shown per side leg panel 18. The elastic strands 20 could be yarns of natural or synthetic rubber latex, or synthetic elastic materials such as spandex. The choice of elastic materials is not limited to elastic strands, but may also include ribbons of elastic materials, elastomeric films, elastic scrims, elastic and nonwoven composites and the like.

FIG. 3 is a cross-sectional view of the embodiment of FIG. 1 and FIG. 2 wherein the backsheet material 12 is represented as a laminate of an air porous or air non-porous, fluid impermeable, polyethylene or polypropylene film 52 and a fluid impermeable polypropylene nonwoven 54. Such materials are known to those skilled in the art as clothlike or textile backsheet. It is also suggested that the backsheet material 12 can be a single layer of polyethylene film or other suitable composite material.

The fasteners 16 of the present invention may involve pressure sensitive adhesive fastening tapes which secure to a frontal portion of silicone, "release" coated polyolefin film, hook and loop tapes or any other suitable fastening medium. The absorbent article may also have an elasticized waistband using an elastic foam, elastic film, elastic strands or other suitable elastic, elastic laminate, stretchable material affixed to or between the coverstock and backsheet portions.

The disposable absorbent article according to the present invention provides a close fitting seal around the thighs of the user, thereby significantly improving its leakage prevention capability. The close fitting seal of the inventive garment is further enhanced through addition of fastening element 16. The fastening element 16 may be provided by known adhesive elements or hook fastening devices. The hook fastening element may be selected so as to be engageable with the loops formed on the surface of a nonwoven fabric. Thus, the nonwoven material of the stretchband panel provides the loop element of a hook and loop fastening system similar to those generally known in the art.

In further embodiments, a loop landing tape may be located near the front waist region of the outside face of the inventive article, and a pair of hook fastening elements may be located in the rear non-elasticized zones of each stretch panel. The fastening portion is therefore attached directly to the central body rather than to the front edge of the stretch panel. The loop landing tape may be constructed from a knitted, extruded, or non-woven material, as is generally known in the art.

Figure 4:
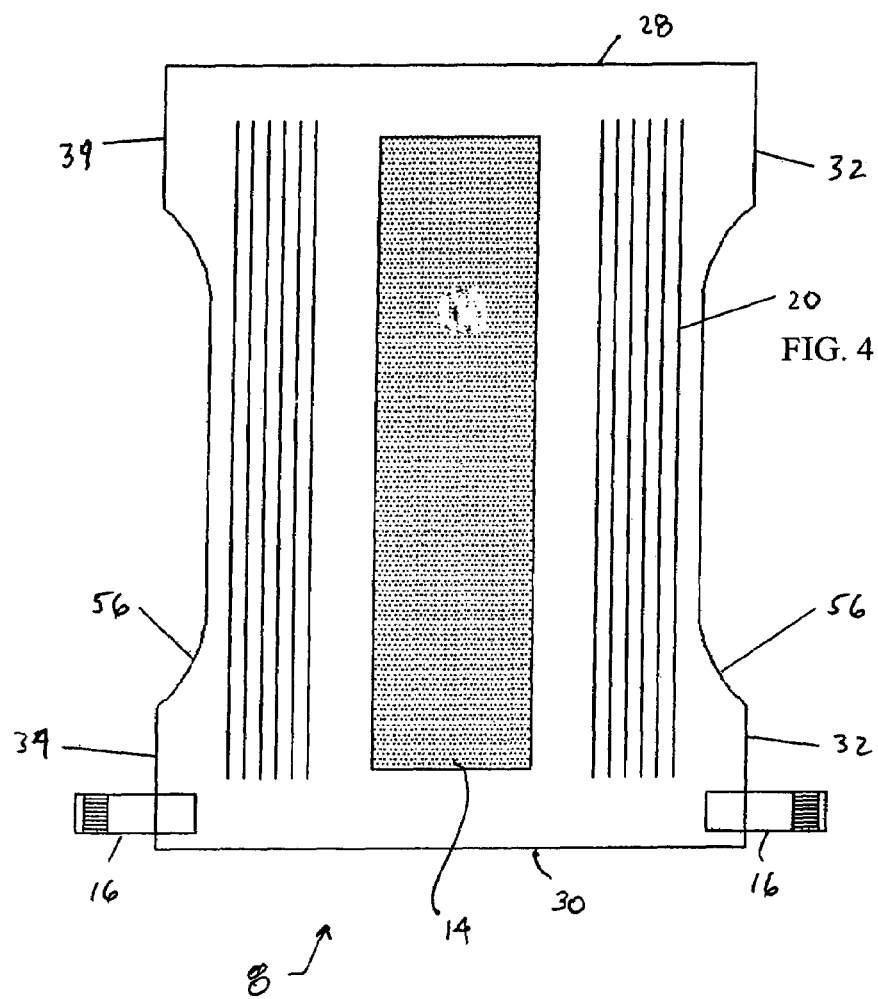
FIGS. 4 and 5 are alternate embodiments of an absorbent article in accordance with the present invention.
Figure 5:
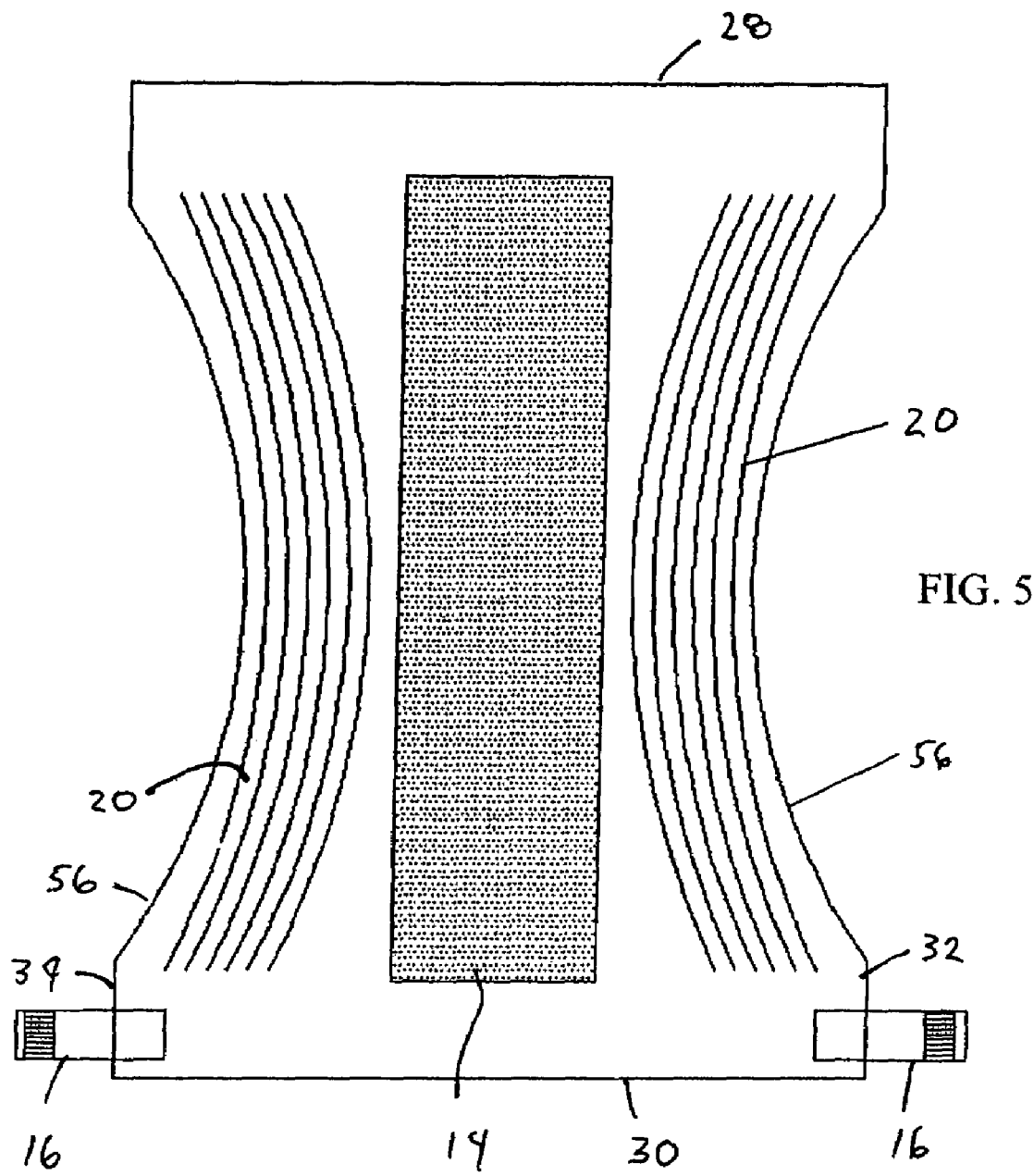

FIGS. 4 and 5 show various other embodiments of absorbent articles 8 according to the present invention. FIG. 4 shows an alternative embodiment where the lateral side edges 32, 34 of the absorbent article 8 are inwardly curved to define cut-out regions 56. This shaped product facilitates a better fit of the product around the waist of the wearer without increasing the amount of material within the side panel that would be gathered around the user's legs when worn.

FIG. 4 discloses elastic elements 20 which are oriented parallel to at least a portion of the lateral side edges 32, 34 of the absorbent article 8. In comparison, FIG. 5 demonstrates still a further embodiment of this invention where the elastic elements 20 follow the inwardly curved side portions of the absorbent article.

Figure 6:
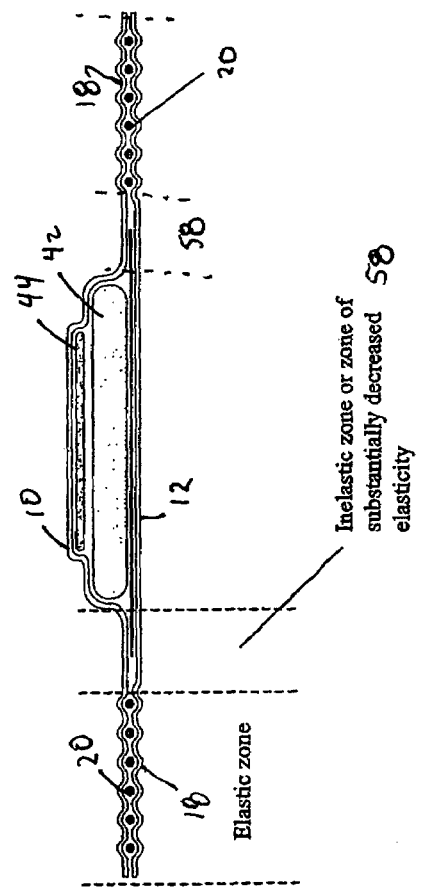
FIG. 6 is a cross sectional view of an absorbent article according to the present invention.
Figure 8:
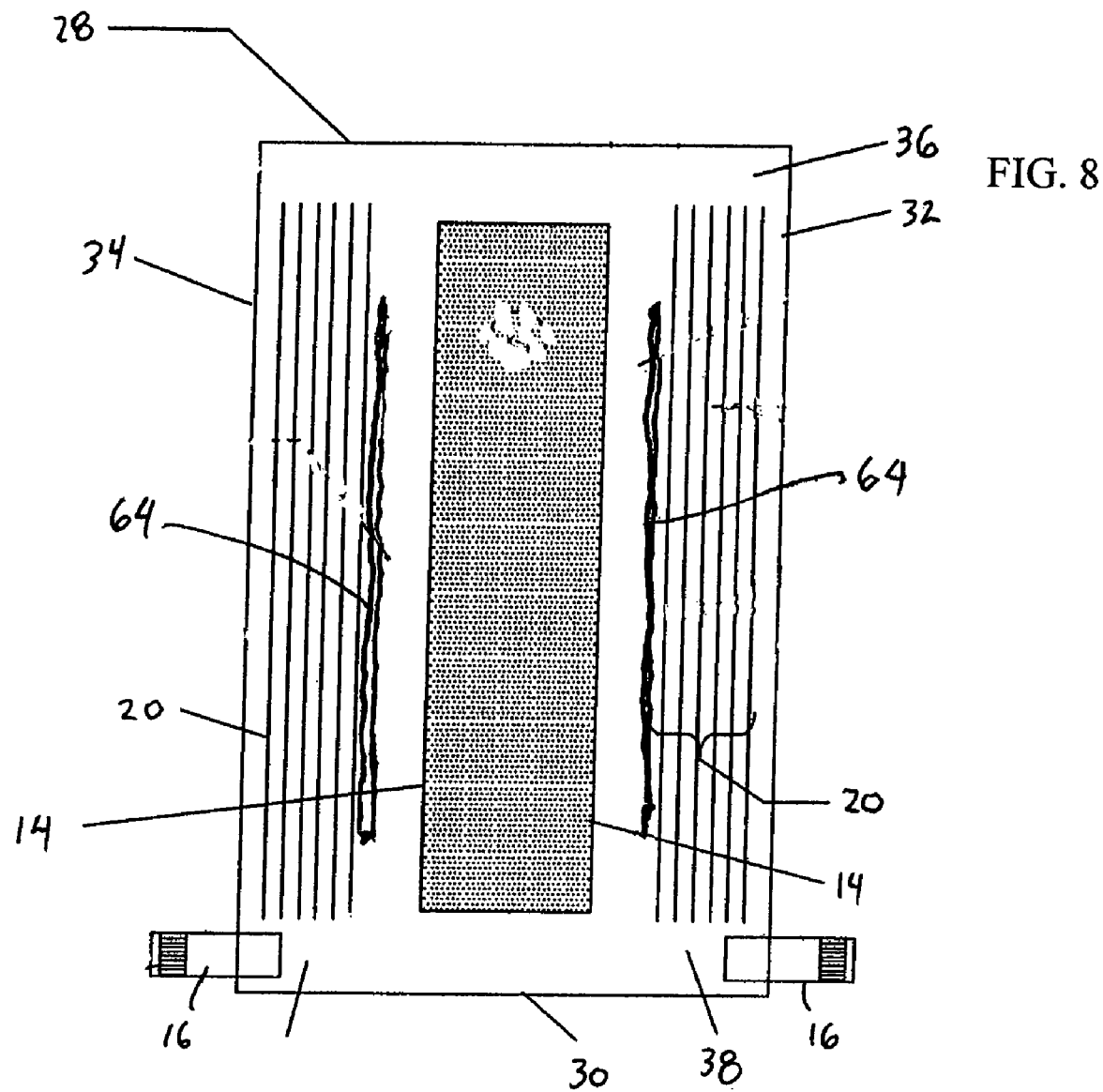
FIG. 8 is a plan view of another embodiment of the present invention.

Additional concepts of the present are disclosed in FIG. 6 wherein the absorbent article 8 is defined by a central absorbent core assembly 14 and a pair of leg wraps 18 separated from the absorbent core assembly 14 by inelastic regions or zones 58 of substantially decreased elasticity 58. Each inelastic zone 58 is defined between the absorbent core assembly 14 and the nearest elastic strand member 20 of the leg wraps 18.

Figure 7:
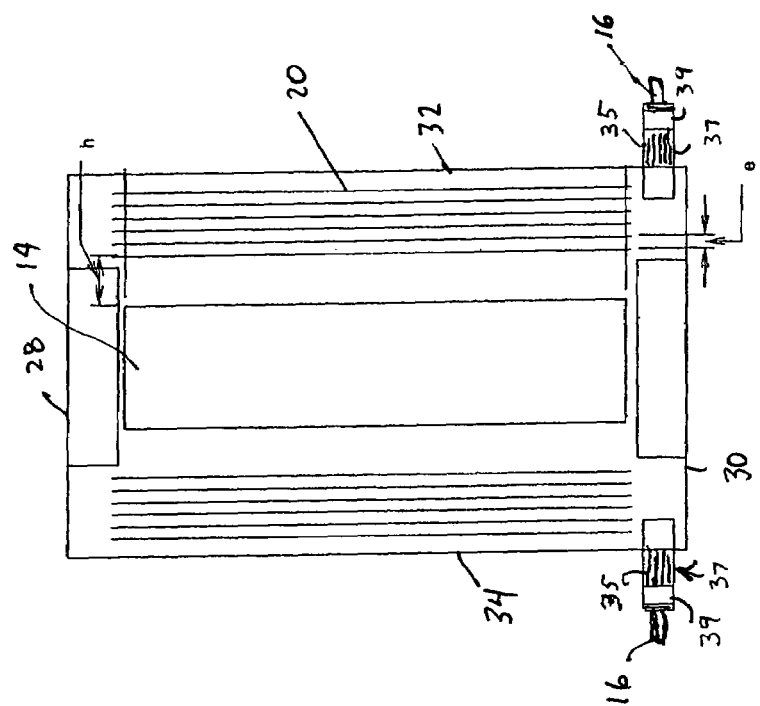
FIG. 7 is a plan view of an absorbent article of an embodiment of the present invention.

Referring to FIG. 7, various dimensions of an absorbent article 8 are illustrated. A distance, h, is defined between the lateral edges of the absorbent core assembly 14 and the elastic strand 20 nearest to the core assembly 14 or stated another way, the strand 20 furthest from the lateral edges 32, 34 of the absorbent article 8. The spacing between the strands 20 of elastic material is represented as distance, e.

FIG. 7 also illustrates another embodiment of the fasteners 16 which may be utilized in the practice of the invention. Fasteners 16 may be provide on the outward portion of side panels 35 having one or more regions of elasticity 37 and one or more regions of inelasticity 39. Other fasteners and side panel constructions are disclosed in U.S. Ser. No. 11/113,114, entitled "Extensible Side Panels For Use With Convertible Absorbent Articles", hereby incorporated by reference and made a part of the present disclosure.

In preferred embodiments of the present invention, the strand 20 count for each elastic leg wrap 18 ranges from 4 to 10 strands, and more preferably between 4 to 6 strands. The distance, h, (width of inelastic zone 58) is preferably between 19 mm to 64 mm, and more preferably between 25 mm to 40 mm. The distance, e, between the strands 20 is preferably between 4 mm to 40 mm, more preferably greater than 6 mm, and yet more preferably approximately 8 mm.

Leg cuff elements 64 may be provided upon a top surface of the coverstock 10 of an absorbent article 8. Leg cuff elements 64 may be defined by material of the coverstock layer 10, or may be of different material attached in know manners to the top surface. The construction of leg cuff elements 64 within the absorbent article 8 would be understood by those of ordinary skill in the art. As depicted in FIGS. 8-13, leg cuff elements 64 may be provided at different distances away from absorbent core 14.

Figure 9:
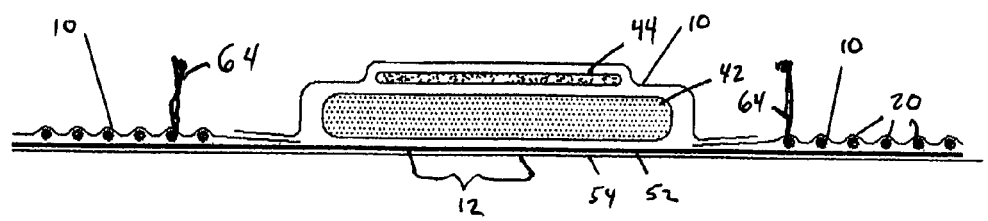
Figure 10:
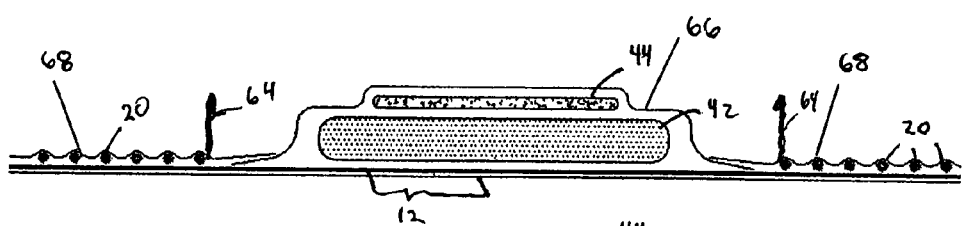

FIGS. 9-24 show cross sections of alternate embodiments of the invention. In some embodiments, the continuous full width nonwoven coverstock 10 may be replaced with a three-piece construction. In the central region 10 of the absorbent article a material 66 permeable to aqueous fluids such as a hydrophilic treated polypropylene nonwoven is placed over the absorbent core to contain the absorbent materials and to allow the passage of urine into the absorbent core 14. Another material element 68 forms the top layer of the elastic side panels 18 along each lateral side edge of the article. This material may be selected from suitable materials such as water permeable polypropylene nonwovens, water impermeable polypropylene nonwovens, polyethylene film and the like. FIG. 9 shows the absorbent core covering material 66 overlapping the outer elastic composite covering material 68. FIG. 10 shows the absorbent core covering material 66 underlapping the material 68 covering the elastic composite.

Figure 11:
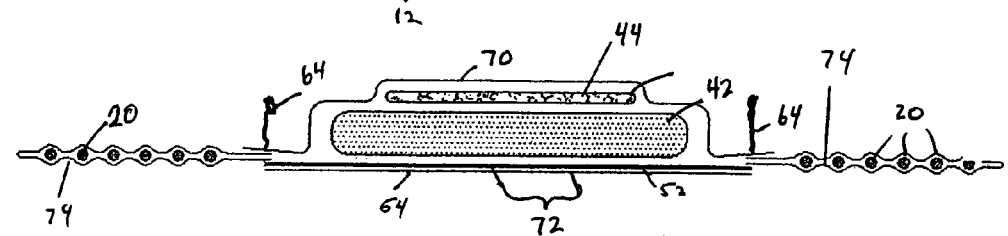

FIG. 11 shows a further embodiment of this invention. In this embodiment an absorbent core assembly 42 is enclosed by a nonwoven, fluid permeable coverstock 70 and a fluid impermeable backsheet 72. In this embodiment the coverstock 70 and backsheet 72 do not extend to the outer edges of the absorbent article. A single ply of nonwoven web 74 is folded around and encloses the elastic strands 20. This elastic composite is then attached to the sides of the absorbent core assembly 14 using any suitable means, for example using hotmelt adhesives or ultrasonic bonding.

Figure 12:
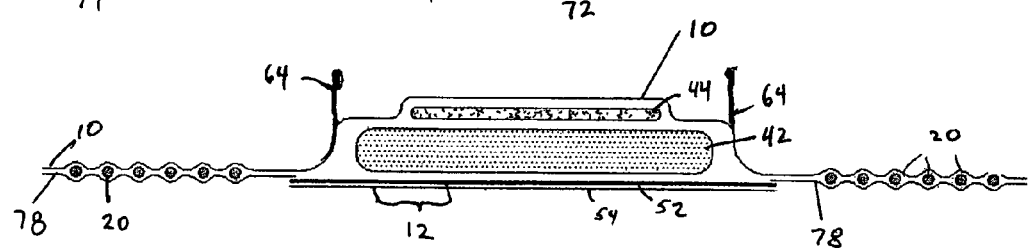

FIG. 12 shows still a further embodiment of the invention, in this example the coverstock material 10 extends continuously over the full width of the absorbent article 8, as is the case in the first embodiment of the invention. In this embodiment a separate piece of suitable material 78 is used to enclose the underside of elastic composite on each leg wrap 18.

Figure 13:
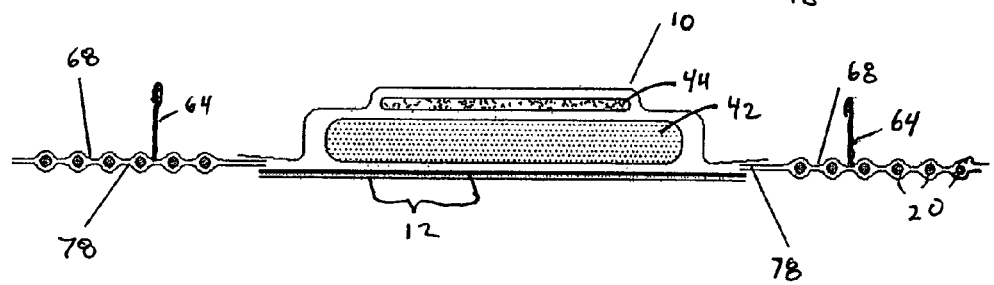
Figure 14:
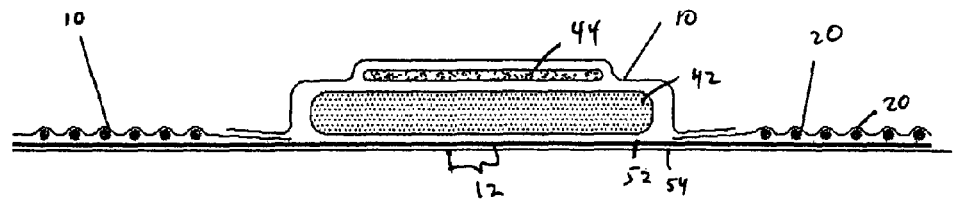
Figure 15:
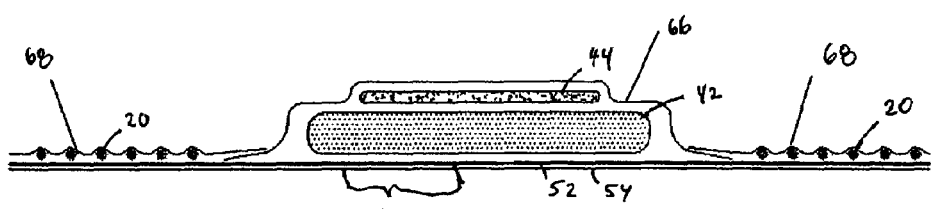
Figure 16:
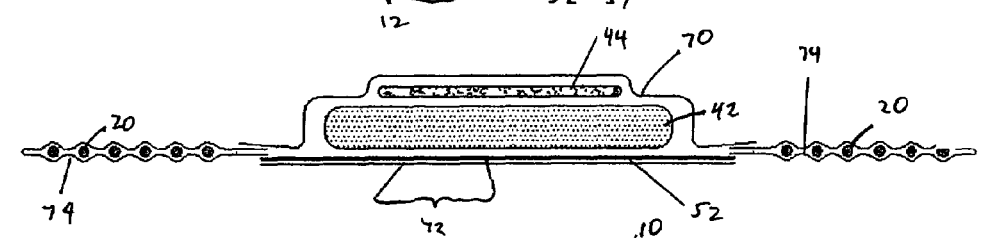
Figure 17:
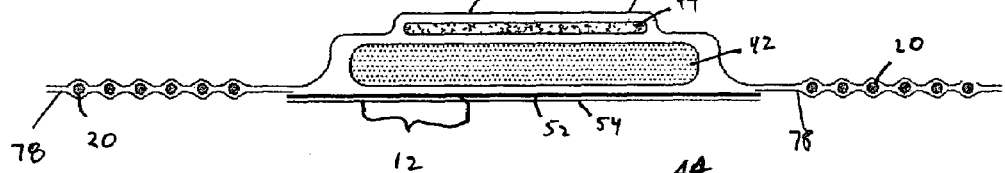
Figure 18:
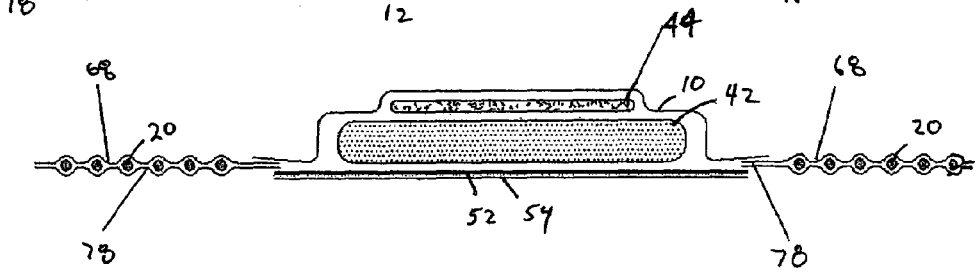
Figure 19:
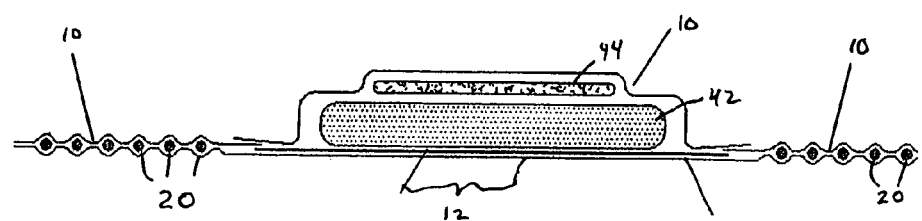
Figure 20:
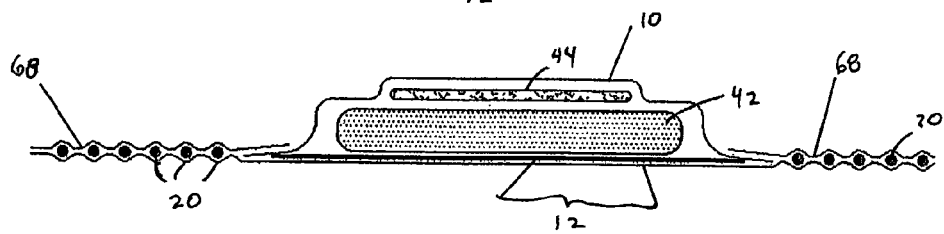
Figure 21:
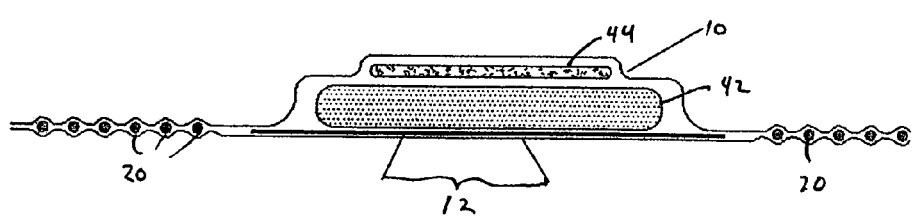

FIG. 13 shows an alternate embodiment to that shown in FIG. 11. This embodiment differs in that two separate layers of suitable material are used to enclose the elastic strand elements 20 within elastic composite elements which are affixed between the coverstock and backsheet portions of the core assembly 14.

FIGS. 14-24 show still further embodiments where the underside of the elastic composite side panels are formed from a material such as the fluid impermeable polypropylene nonwoven which extends continuously across the full width of the absorbent article.

FIGS. 25-28 depict a disposable absorbent article of the present invention as fitted to the wearer. The absorbent article 8 folds inwards at point 80 and outwards at point 82. The absorbent article 8 may naturally conform to the shape depicted in FIGS. 25-28. It may be necessary or useful to prefix the article in this configuration by applying spots of adhesive 94 (FIGS. 29-33), or by using any other suitable means to ensure that the article is fitted correctly to the wearer.

The outcome of this folding pattern of the article is two fold. First, the elastic leg wraps 18 are desirably positioned against the wearer's body and fit securely around the upper thighs and buttocks of the user. This serves to create a generally fluid impermeable seal around the legs, crotch and thighs of the user, which reduces the incidence of leakage. Second, the absorbent core assembly 14 is held away from the body of the wearer, particularly in the crotch area of the article. This serves to create a void space 84 between the user's body and the absorbent core assembly 14.

Figure 25:
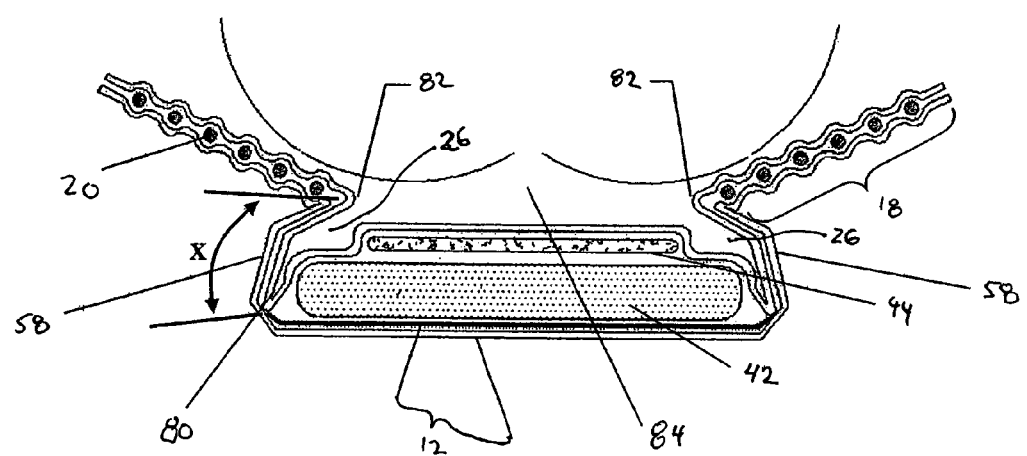
FIG. 25 is a depiction of the application of an absorbent article of the present invention upon a wearer.
Figure 26:
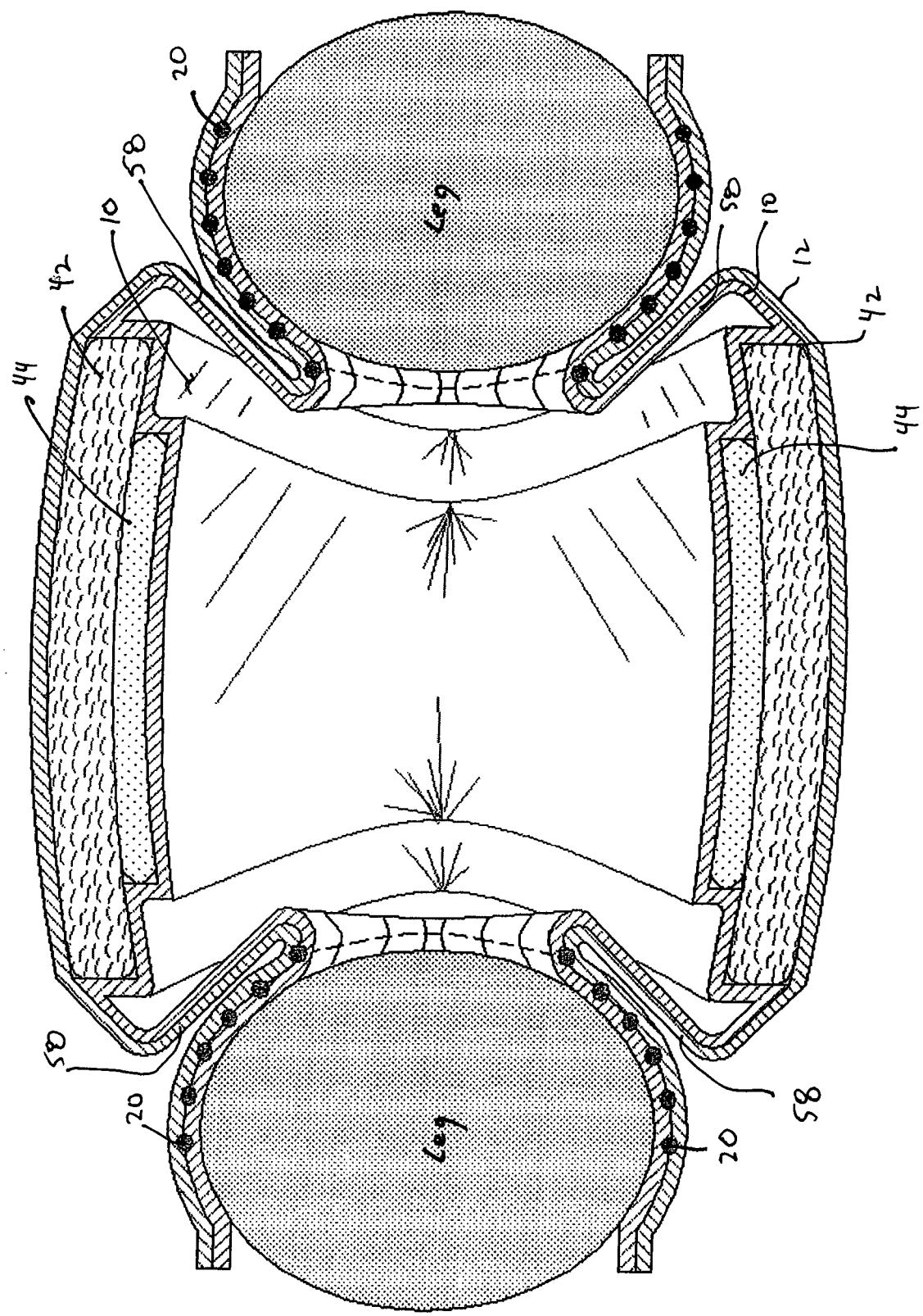
FIGS. 26 and 27 are depictions of cross-sections taken through an absorbent article and wearer.
Figure 27:
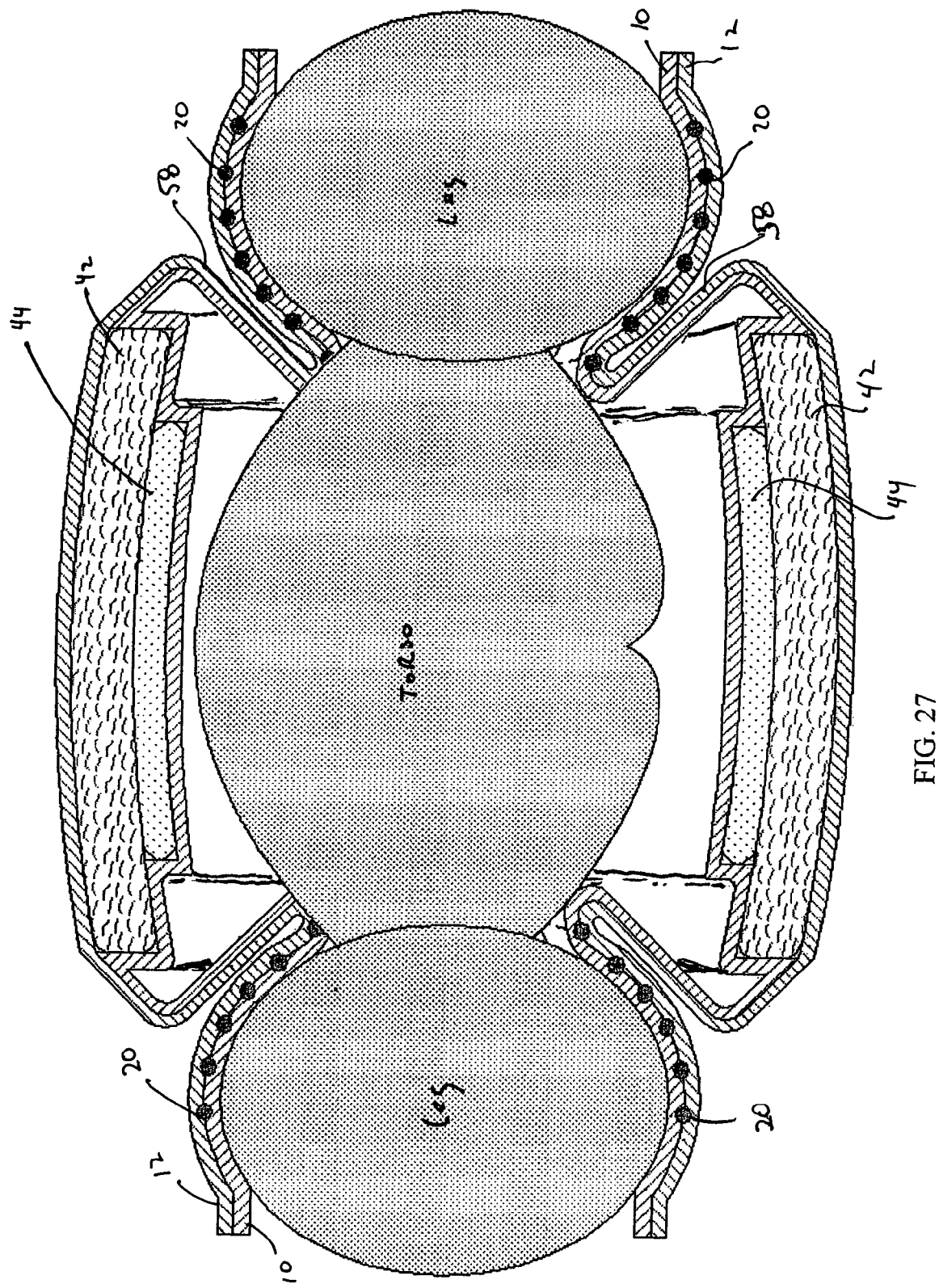

This void space 84 may have an approximately trapezoid appearance as demonstrated in FIG. 25, with a base having a length approximately equal to the width of the absorbent core 42, sides of a length approximately equal to dimension X, and a top length dependent upon the angle formed between the base and sides. Portions of the article 8 can pivot or rotate relative to each other so that the absorbent core 42 and leg wraps 18 can freely move upon the wearer. This pivoting effect enables the leg wraps 18 to move during use while maintaining an effective leg seal.

Void space 84 created by the structure of the absorbent article 8 serves to hold the absorbent core 42 away from direct contact with the skin or body of the wearer. For example, rewet or the wetting of the user's skin by body waste fluids not completely captured by the superabsorbent materials within the absorbent core 42 is reduced, resulting in improved comfort for the wearer.

Figure 28:
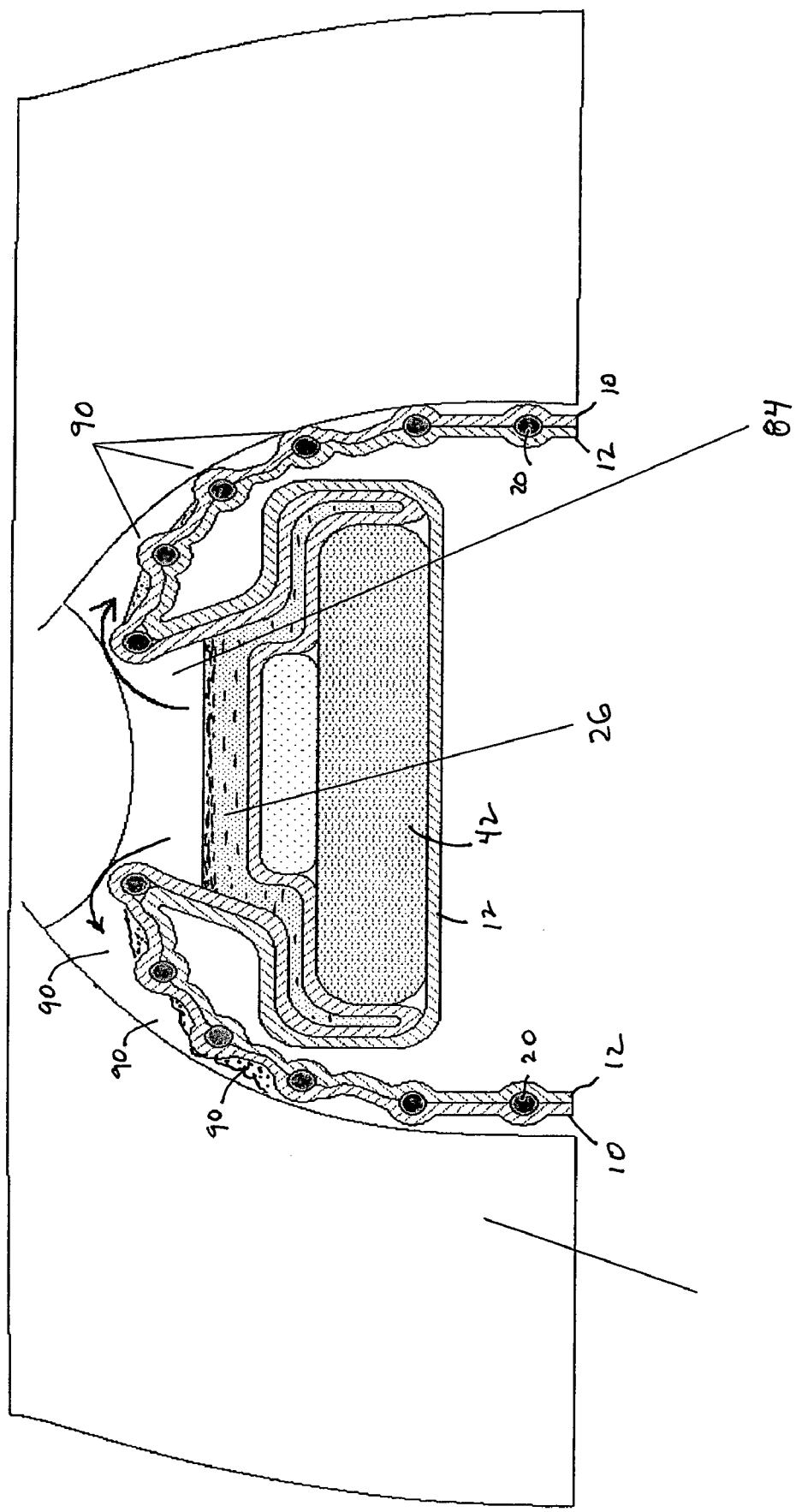
FIG. 28 is a depiction of the absorbent article upon a wearer.

Referring particularly to FIGS. 25 and 28, reservoir 26 is a structure in which body exudates can be collected, contained and held. Exudates float or flow along the top surface flow into and down the side walls of the reservoir 26 to be collected in the bottom of the reservoir 26 until the absorbent article 8 can be removed. The reservoir 26 is, therefore, especially effective for exudates, particularly loose fecal materials, that are not easily absorbed by the absorbent core 14 and tend to "float" on the coverstock 10.

The reservoir 26 may be disposed at least in part between the elastic members 20 and the longitudinal centerline of the absorbent article 8, e.g., by material within the zone of decreased elasticity 58. The reservoir 26 may be constructed of materials known in the art which are compliant and conformable enough to present a pocket or well-like shape. The material may be absorbent, wicking or impermeable to exudates. For example, the reservoir 26 may comprise an element (i.e., the coverstock 10, the backsheet 12 or the leg wrap 18) or any combination of these elements or other elements of the absorbent article 8 configured or folded to present a reservoir. In addition, the reservoir 26 may have a variety of shapes and cross-sections provided that a pocket or well-like shape is formed to contain and hold the exudates. For example, the reservoir 26 may have a semi-circular, square or parabolic cross-section.

Preferably, the reservoir 26 is formed by folding material within the zone of decreased elasticity 58 and securing the folded portion to portions of the coverstock 10 adjacent the absorbent core 14. FIGS. 24 and 25 illustrate cross-sectional views of an absorbent article according to the present invention. FIGS. 24 and 25 are cross-sectional views of the absorbent article taken along transverse planes of the user a horizontal plane at right angles to a vertical sagittal plane which divides the body into superior and inferior parts.

FIG. 28 illustrates the temporary reservoir 26 and void 84 wherein the reservoir 26 contains fluid prior to absorption by core 14. Fluid is prevented from passing through side leg panels 18 by the series of elastic gathers defining a plurality of fluid dams as indicated by numeral 90. Fluid which passes through one of the fluid dams 90 encounters the furtherlyoutward fluid dam 90. As a result, multiple sealing structures are provided by the leg wraps 18 of the present invention.

Figure 29:
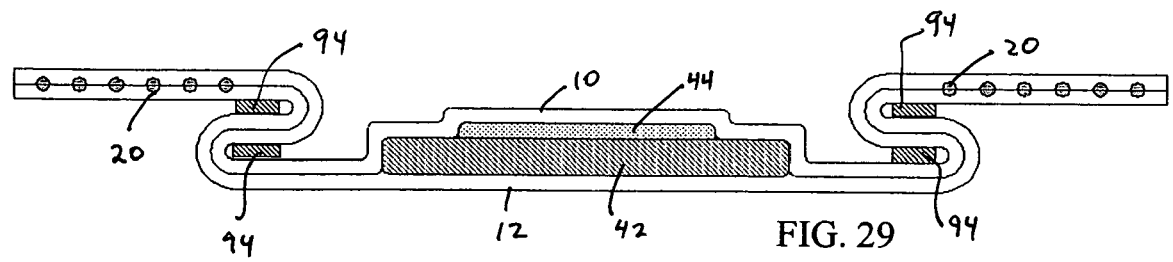
FIG. 29 is a cross-sectional view illustrating a folded side panel concept in accordance with the present invention.

It has been found that the desired trapezoid shape of void 84 and/or reservoir 26 can be difficult to form and maintain in every application as it can be dependent on how the absorbent article 8 is placed on the user and movements the user might make whilst wearing the diaper. In order to improve the likelihood that this shape exists in the product when the diaper is fitted to the wearer and to improve the stability of the desired shape during use it is possible to pre-fold the diaper in the side regions of the product, and fix the fold with the addition of a bonding element. This bonding element could be any combination of adhesive, thermo-bonding, ultrasonic bonding or any other suitable method of bonding plastic and nonwoven based materials. It is also envisage that this fold-fixing bond point could also be obtained using a hook and loop engagement system or other non-permanent fixation means In some embodiments of the present invention a z-shaped fold is formed in the leg wrap 18 of the diaper during manufacture. The leg wraps 18 can be folded in towards the core and a suitable bonding method is then used to fix this fold in position. Secondly, the side panel is then folded back away from the core. An optional bonding method can be used to fix this fold in position. FIG. 29 shows a cross-section of the folded diaper with the fold-fixing bonded areas indicated as numeral 94. Bonded areas 94 are optional and embodiments of the present invention may not necessarily include bonded areas 94. Similarly, other embodiments of the present invention may include one or more bonded areas 94.

Figure 30:
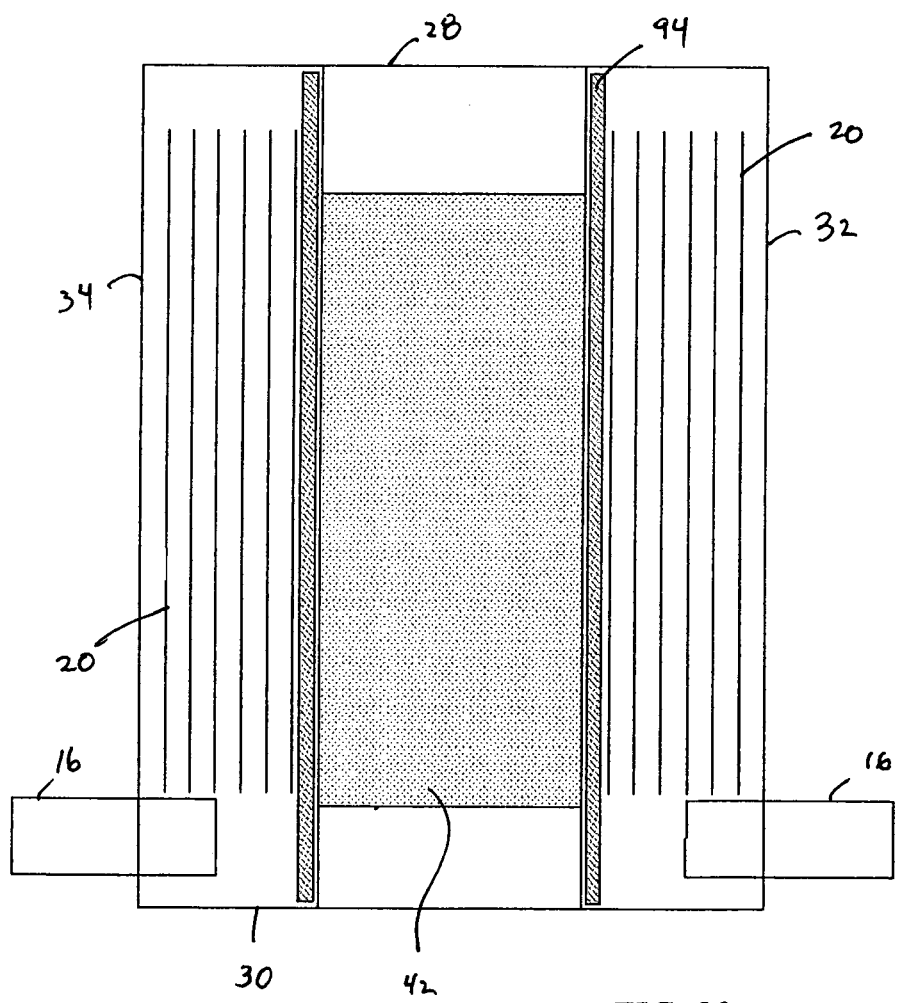
FIGS. 30-33 illustrate different embodiments of securing the folded side panel in accordance with the present invention.
Figure 31:
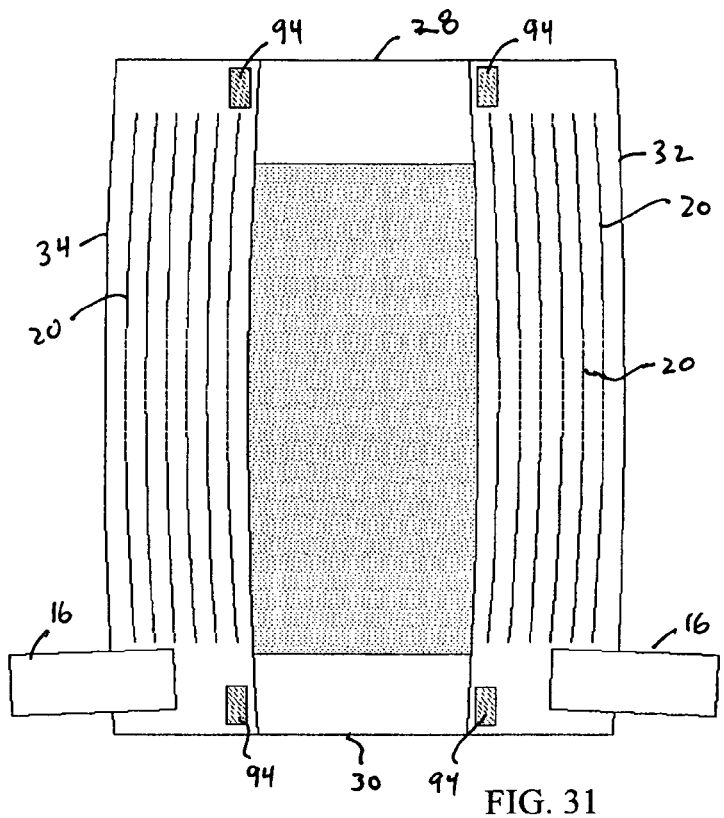

Bonding of the folded side region can be achieved by a longitudinally continuous application of adhesive using any suitable application method, such as spiral spray, intermittent bead or continuous bead. Alternatively a continuous line of an ultrasonic or thermal bonding method could be used. FIG. 30 shows a diagram of this embodiment.

Figure 32:
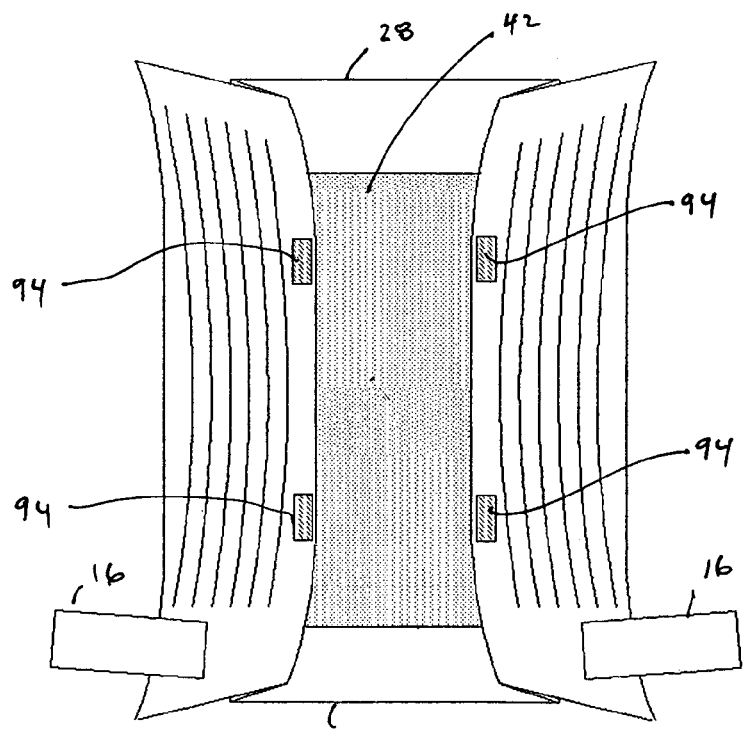
Figure 33:
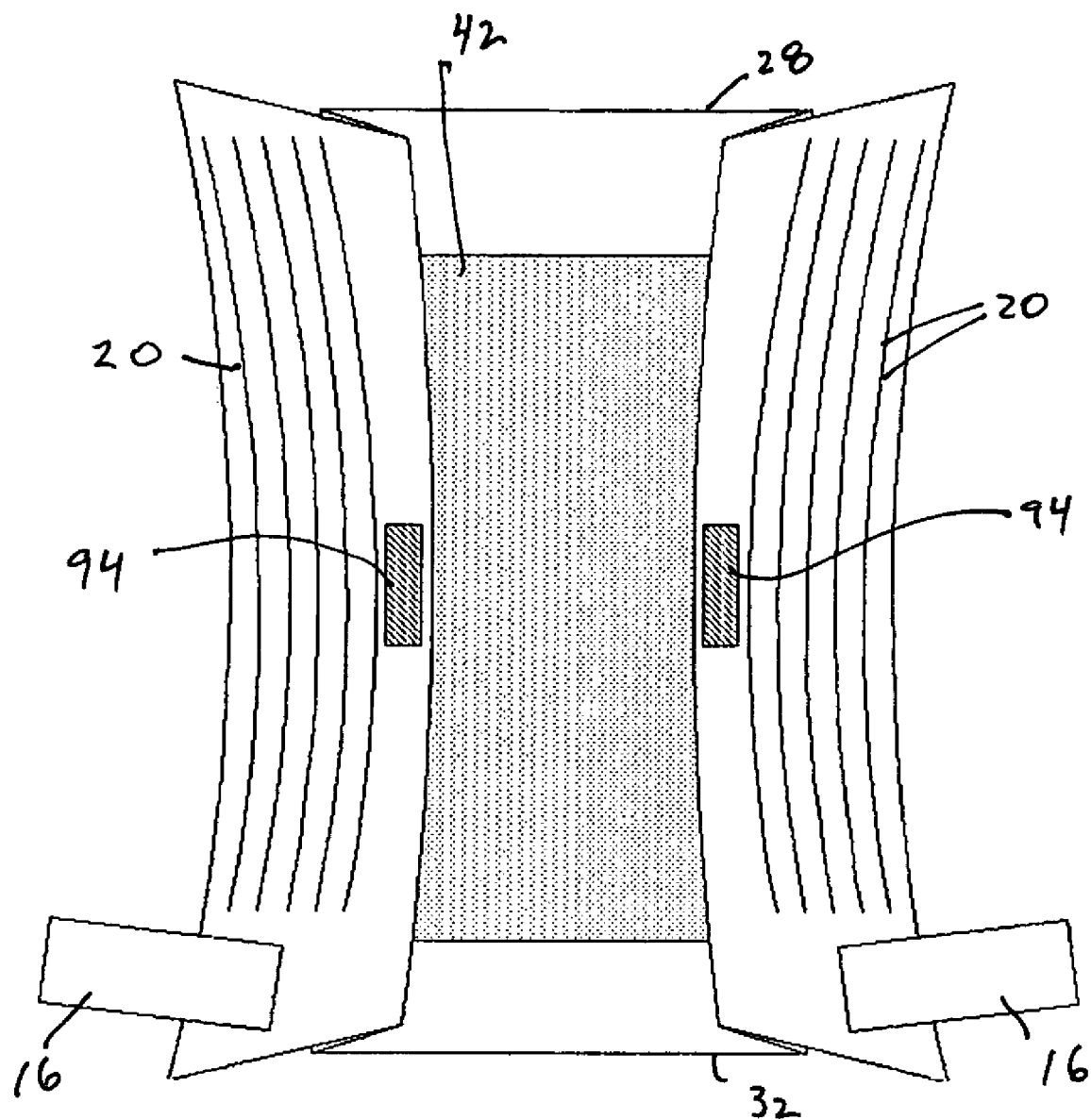

In further embodiments of this invention the longitudinal fold-fixing bonding points can be discontinuous. This has the advantage of allowing selection of zones on the diaper where the fold can open up to provide maximum void space, whilst effectively pinning the fold in position in other selected areas. In the embodiment of FIG. 32, two fold fixing bond points per side panel 18 are provided in a region close to the front and rear edges of the diaper. In another embodiment of FIG. 32 these bond points are moved towards the centre of the diaper. In yet another embodiment of FIG. 33, a single bond point per side panel is provided in the center crotch region of the diaper.

The diagrams above show possible variations of the folded chassis of this invention and the possible positions for fold-fixing bond points. However further embodiments of this invention not shown by the drawings above are also possible. The position of the fold is variable and could be moved laterally to any position within the side panel or, alternatively, sections of the absorbent core could be incorporated into the folded region. The number of fold-fixing bond points per side panel is also variable.

It is important that the tension forces provided by the elasticized side leg panel 18 are neither too low nor too high. If the tension forces provided by the side leg panel 18 are too low, the absorbent article 8 may not fit very closely in certain regions around the legs and the waist and the absorbent article ability to prevent leakage will be compromised. High tension forces may constrict the user's thighs and cause discomfort. In a typical prior art disposable absorbent article, the positioning of elastomeric elements and the type of elastomeric element placed does not vary along the length of the stretch panel. The elasticity or elastication of the stretch panel is, therefore, uniform along the stretch panel length. When elongated in a uniform manner, the overall tension provided by the stretch panel is also uniform along its length. The magnitude of this uniform tension depends on the overall elongation of the leg wraps 18. When the absorbent article 8 is worn, however, the elongation of the leg wrap 18 along it length is generally non-uniform, and thus, the tension generated varies. As a result, there may be regions about the length of the leg wrap 18 that are undesirably too loose or too tight.

In one respect, regions or zones devoid of elastic elements—e.g., zones provided for finger lift area and landing area—are also distinct regions of elasticity formed by pre-determined placement of elastic elements. These regions of elasticity differ, however, in the sense that the elastic elements do not impart elasticity to the stretch panel in these regions in contrast to the distinct regions of imparted elasticity in the vicinity of the elastic elements. Descriptions of some configurations suitable for use with the present invention are found in U.S. Ser. No. 10/441,469, entitled "DISPOSABLE ABSORBENT ARTICLE WITH ELASTICIZED SIDE PANELS, AND METHOD OF MAKING THE SAME", hereby incorporated by reference and made a part of the present disclosure.

In addition, embodiments of the absorbent article 8 achieve increased comfort by positioning the elasticized side flaps closer to the side edge of the absorbent core 42. Thus, when initially placed on the wearer, the elasticized side flaps ride in the groin areas along the inner thighs of the wearer thereby providing a better initial fit. This positioning provides a better initial fit on the wearer because elasticized side flaps of conventional diapers are often initially positioned farther down on the thigh of the wearer and subsequently tend to ride or creep up into the groin regions of the wearer during use. Because the side flaps are drawn up, gaps tend to form in the legs and waist providing less comfort for the wearer. However, because the present invention initially positions the elasticized leg wraps 18 in the groin areas, sagging of the diaper is reduced resulting in increased comfort for the wearer.

The foregoing description of the present invention has been presented for purposes of illustration and description. It is to be noted that the description is not intended to limit the invention to the various apparatus and processes disclosed herein. Various aspects of the invention as described above, may be applicable to other types of disposable absorbent articles and garments, and processes for making the same. For example, the feature of an elasticized side panel having the fastening portion described above, may be incorporated in other disposable absorbent articles such as training pants, etc. Moreover, the feature of an elasticized side panel as having the characteristic elasticity described above may also be incorporated in other disposable absorbent articles and garments. Such variations of the invention will become apparent to one skilled in the relevant consumer products, or other relevant art provided with the present disclosure. Consequently, variations and modifications commensurate with the above teachings, and the skill and knowledge of the relevant art, are within the scope of the present invention. The embodiments described and illustrated herein are further intended to explain the best modes for practicing the invention, and to enable others skilled in the art to utilize the invention and other embodiments and with various modifications required by the particular applications or uses of the present invention.

What is claimed is:

1. A disposable absorbent article comprising:
    a) an absorbent core disposed between a liquid pervious top sheet and a liquid impervious back sheet;

b) a pair of flexible leg wraps extending outwardly from and along side edges of said absorbent core, the flexible leg wraps being adapted to wrap around a wearers legs;

c) a plurality of spaced-apart elastic strands within the pair of flexible leg wrappings, wherein an inelastic zone of the pair of flexible leg wrappings extends outward from the longitudinal edge of the absorbent core, the longitudinal edge of the absorbent core defines an inner boundary of the inelastic zone and a first elastic strand within the pair of flexible leg wrappings defines an outer boundary of the inelastic zone, wherein the leg wraps and absorbent core are capable of forming a reservoir with a plurality of fluid dams that are defined at least in part by the plurality of elastic strands during use of the absorbent article, wherein each fluid dam is capable of capturing a volume of liquid waste from passing through the leg wrap, wherein when the absorbent article is disposed in a relaxed, generally flat, open condition, the inelastic zone extends outwardly away from a longitudinal edge of the absorbent core and the first elastic strand defining the outer edge of the inelastic zone is the closest elastic strand to the longitudinal centerline of the body, wherein the distance between the absorbent core and the nearest strand of elastic is between 19 mm to 64 mm, the number of elastic strands per side panel region is between 4 and 10 strands, and a distance between the individual elastic strands is between 4 mm to 30 mm; and, wherein when the absorbent article is disposed in a relaxed, generally flat, open condition, the flexible leg wrappings extend from the lateral edge of the absorbent core to the longitudinal periphery edge of the article in a single plane and wherein the plurality of elastic strands are disposed within the single plane occupied by the flexible leg wrappings.

2. The absorbent article of claim 1 wherein the distance between individual elastic strands is between 6 mm to 8 mm.

3. The absorbent article of claim 1 wherein the distance between the absorbent core and the nearest strand of elastic is between 25 mm to 40 mm.

4. The absorbent article of claim 1 wherein the inelastic zone is capable of being folded over to define portions of the reservoir.

5. The absorbent article of claim 4 wherein portions of the inelastic zone are adhered together in one or more locations of the absorbent article.

6. The absorbent article of claim 1 wherein a distance between adjacent pairs of elastic strand is nonuniform so that the elastic strands are not equally spaced apart.

7. The absorbent article of claim 6 wherein the elastic strands are provided with a plurality of different diameters.

8. The absorbent article of claim 7 wherein the distance between the central absorbent core and the nearest strand of elastic is between 30 mm to 44 mm.

9. The absorbent article of claim 7 wherein the number of elastic strands is between 6 and 8 strands.

10. The absorbent article of claim 7 wherein the distance between the individual strands is between 6 mm to 9 mm.

11. The absorbent article of claim 10 wherein the distance between the absorbent core and the nearest elastic strand is between 42 mm to 50 mm.

12. The absorbent article of claim 7 wherein the distance between the absorbent core and the nearest elastic strand is between 10 mm to 100 mm.

13. The absorbent article of claim 1 wherein the top sheet has zones of differing hydrophilic properties.

14. A disposable absorbent article comprising:

an absorbent core being disposed between a liquid pervious top sheet and a liquid impervious back sheet; and a pair of elasticized leg wraps extending longitudinally adjacent opposite lateral sides of said absorbent core, said leg wraps including a plurality of spaced-apart elastic strands, wherein in a relaxed state prior to use, said leg wraps extend outwardly away from said absorbent core in an unfolded manner, and an outer strand of said leg wraps is further away from a longitudinal centerline of the absorbent core than an inner strand, wherein during use a reservoir is defined by the absorbent core and folded portions of the leg wrap during use, and a plurality of fluid dams are defined in part by the plurality of spaced-apart elastic strands during use, with each of the plurality of fluid dams capable of retaining a fluid volume against leakage from the leg wraps, and with the absorbent article provided in a generally flat, opened orientation, the distance between the absorbent core and the nearest strand of elastic is between 25 mm to 51 mm, the number of elastic strands is between 5 and 10, and the distance between the individual strands is between 5 mm to 10 mm wherein when the absorbent article is disposed in a relaxed, generally flat, open condition, the flexible leg wrappings extend from the lateral edge of the absorbent core to the longitudinal periphery edge of the article in a single plane and wherein the plurality of elastic strands are disposed within the single plane occupied by the flexible leg wrappings.

15. The disposable absorbent article of claim 1 or 14, optionally further comprising a leg cuff, wherein said leg cuff is inelastic when present.

16. The disposable absorbent article of claim 1 or 14, wherein the disposable absorbent article lacks any leg cuff.

* * * * *